United States Patent [19]

Hahn et al.

[11] Patent Number: 5,217,014
[45] Date of Patent: Jun. 8, 1993

[54] DEPOLARIZED PRE-GELLED ELECTRODES

[75] Inventors: Steven Hahn, East Hampton, N.Y.; Mark L. Faupel, Conyers, Ga.

[73] Assignee: Biofield Corp., New York, N.Y.

[21] Appl. No.: 787,641

[22] Filed: Nov. 4, 1991

[51] Int. Cl.[5] ............................................. A61B 5/04
[52] U.S. Cl. ..................................... 128/640; 128/641
[58] Field of Search ............... 128/640, 639, 642, 644, 128/798, 670, 641, 802, 803; 206/328

[56] References Cited

U.S. PATENT DOCUMENTS

| | | |
|---|---|---|
| 3,496,929 | 2/1970 | Domingues . |
| 3,868,946 | 3/1975 | Hurley . |
| 4,037,267 | 1/1977 | Kisor ................................ 206/328 |
| 4,270,543 | 6/1981 | Tabuchi et al. . |
| 4,317,278 | 3/1982 | Carmon et al. ................... 128/639 |
| 4,328,809 | 5/1982 | Hirschowitz et al. . |
| 4,365,634 | 12/1982 | Bare et al. ........................ 128/640 |
| 4,377,170 | 3/1983 | Carim . |
| 4,416,288 | 11/1983 | Freeman . |
| 4,486,835 | 12/1984 | Bai et al. . |
| 4,628,937 | 12/1986 | Hess et al. . |
| 4,742,828 | 5/1988 | Sundström ........................ 128/640 |

Primary Examiner—Lee S. Cohen
Assistant Examiner—Marianne Parker
Attorney, Agent, or Firm—Sixbey, Friedman, Leedom & Ferguson

[57] ABSTRACT

The electrode assembly includes at least one pregelled biopotential electrode having an electrolyte gel in contact with the electrode element. An electrically conductive component is removably mounted to electrically connect both the electrolyte gel and the electrode element conductor to complete a conductive bridge therebetween. The conductive element is inert relative to the electrolyte to avoid degradation of the electrolyte.

34 Claims, 1 Drawing Sheet

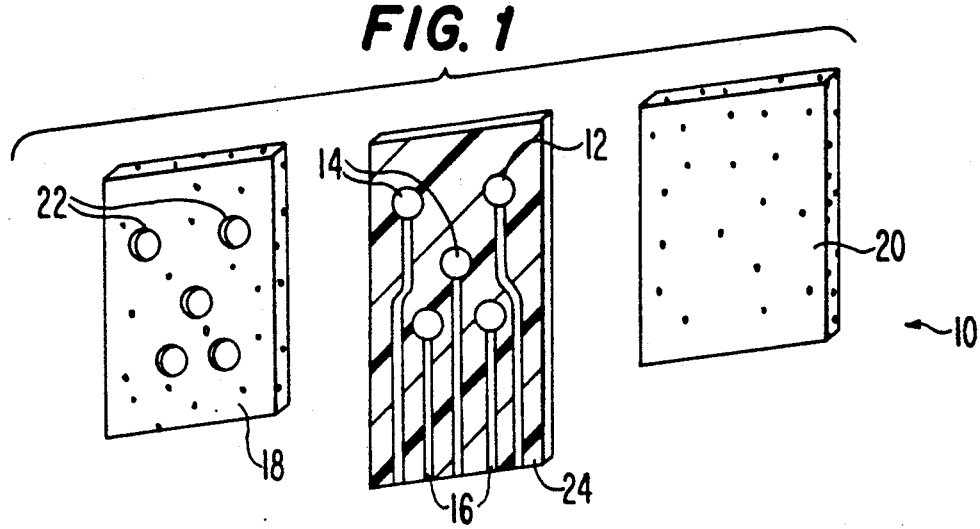
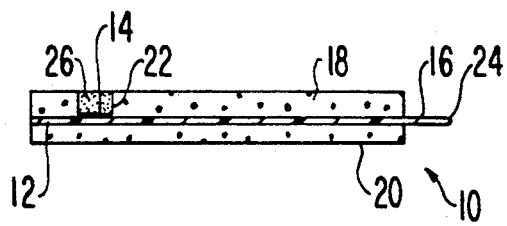 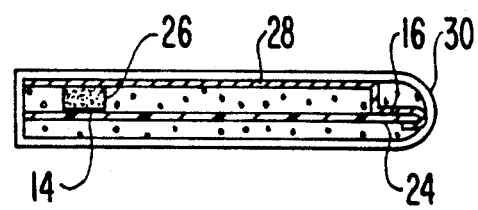
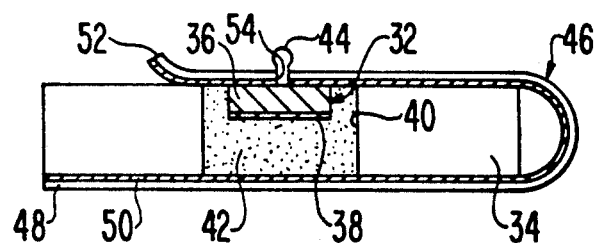
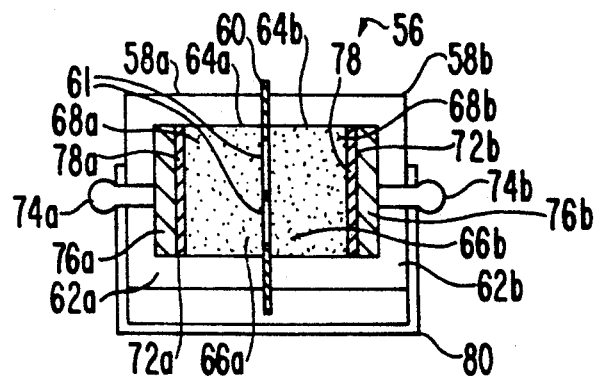

DEPOLARIZED PRE-GELLED ELECTRODES

TECHNICAL FIELD

The present invention relates generally to electrodes for detecting the potential of the electric field present on the tissue or skin of a living organism, and more particularly to a structure which operates to maintain electrodes in a depolarized state prior to use.

BACKGROUND ART

Recent advances in medical technology have often involved the measurement or recording of electrical activity which occurs as a function of underlying biological activity. This in turn has led to considerable research and development in the field of sensing electrodes adapted for use in a number of applications where biopotentials are measured on the skin or tissue of a living organism. Silver-silver chloride electrodes combined with an electroconductive paste or gel have been found to be particularly suitable for biopotential measurements, as illustrated by U.S. Pat. Nos. 4,328,809 to B. H. Hirschowitz, et al. and 4,270,543 to K. Tabuchi et al. Electrodes of this type have been previously assembled in matrix configurations for use in screening and mapping applications as illustrated by U.S. Pat. Nos. 4,416,288 to Freeman, 4,486,835 to Bai and 4,628.937 to Hess et al.

Many electrodes are packaged in a pre-gelled state wherein an electrolytic paste or gel is packaged as part of the electrode. The gel may be located in a central gel reservoir consisting of a molded cup, or it may be contained in a dye-cut hole in a foam which encapsulates a gel saturated open cell compressible foam column, such as shown by U.S. Pat. No. 3,868,946. In most instances, the pre-gelled electrodes are sold ready for use with an electrically conductive material such as metal or a metal chloride in contact with the electrolyte gel.

A pre-gelled electrode system is generally not a battery by itself, but forms a part of a battery-system consisting of two or more electrodes placed on the body. In such a system, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC biopotentials are of interest, artifacts, such as DC offsets, should be reduced to the lowest level. Clearly, pre-gelled electrodes can possibly represent such undesired DC voltage artifact which should be limited to the lowest voltage possible; ideally zero volts. Most pre-gelled electrodes when introduced in the battery system outlined above contribute some unwanted DC voltage (polarization effect) to biopotential measurements. It is important to lower the possibility of such DC artifacts occurring in a degree sufficient to have a substantial adverse effect on biopotential measurements.

It is not feasible, in situ, to measure only the DC contributed by the pre-gelled electrodes when they are placed in a battery system. Instead, manufacturers and researchers have attempted to establish the magnitude of these potentials by mounting two pre-gelled electrodes under test in a back to back fashion with the electrolyte gels of the two electrodes touching and the leads from the electrodes connected to a voltmeter. In fact, this is a fair measurement since the technique does create a battery by using two electrodes and eliminating the body. When pre-gelled electrodes are tested this way, using a high impedance digital voltmeter, DC voltages to approximately 10 millivolts are frequently found.

Many attempts have been made to reduce the polarization effect present in biopotential electrodes. This was first done by modifying the electrode structure in an attempt to avoid dissimilar junction effects as illustrated by U.S. Pat. No. 3,496,929 to F. J. Domingues. Subsequently, an oxidizing agent has been added to the electrolyte gel to reduce the metal on the surface of the electrode sensing element to a metal action which reacts with the anion of the electrolyte to produce an insoluble compound which is deposited on the sensing element to render it non-polarizable. This method of producing a non-polarizable electrode is illustrated by U.S. Pat. No. 4,377,170 to H. M. Carim.

Although the prior art structures for reducing the polarization effect present with biopotential electrodes accomplish this purpose to some extent, they require a basic chemical material change in the electrodes, and do not effectively eliminate offset potentials which can cause a significant error in a biopotential measurement taken with the electrode. Prior art structures do not provide a simple, removable method for depolarizing various types of pre-gelled electrodes. Also, these prior structures do not provide either an efficient or cost effective method for depolarizing a large number of electrodes combined in an electrode mapping or screening matrix.

DISCLOSURE OF THE INVENTION

It is the primary object of the present invention to provide a novel and improved assembly to effectively depolarize single or multiple pre-gelled biopotential electrodes.

Another object of the present invention is to provide a novel and improved removable electrical short circuiting system which effectively depolarizes one or more pre-gelled biopotential electrodes during shipment and storage without causing degradation of the gel.

Yet another object of the present invention is to provide a novel and improved removable electrical short circuiting system which effectively depolarizes one or more pre-gelled biopotential electrodes, bringing each electrode to a stable, near zero DC offset level, until use. This is done by shipping and storing the electrode system electrically shorted before use, at which time the short circuiting system is removed.

Yet still another object of the present invention is to provide a novel and improved pre-gelled biopotential electrode or electrodes having a removable depolarizing structure bridging the electrolyte gel and an electrode terminal or leads. The depolarizing structure is operable to depolarize single electrodes, groups of paired electrodes, and multiple electrodes which are arranged in an electrode matrix.

A further object of the present invention is to provide a novel and improved packaging assembly wherein a single or a plurality of pre-gelled biopotential electrodes are formed in a package with a removable electrical short circuiting package element which effectively depolarizes the electrode or electrodes during shipment and storage, and until use.

Still further object of the present invention is to provide a novel and improved electrode matrix assembly which is formed with a removable depolarizing layer bridging the area between the electrode leads for the assembly and the electrolyte gel. This depolarization layer closes the open end of an insulating cup containing the gel and then extends into contact with the electrode leads or terminals.

These and other objects of the present invention are accomplished by forming a single biopotential electrode or a matrix of such electrodes which is adapted to be stored and shipped in a pre-gelled state with an electrolyte. The electrode or electrode matrix is formed in a manner wherein the electrolyte gel and the contact or contacts for the electrode may be bridged by a shorting element which is removable prior to the use of the electrode or electrode matrix. Preferably, the shorting element consists of electroconductive material, such as wire, strap or electroconductive packaging material, which is removed before the electrode is used. This shorting element can close the open end of a gel-containing opening for an electrode, or may close a plurality of gel containing openings in an insulating face sheet for an electrode matrix.

BRIEF DESCRIPTION OF THE DRAWINGS

FIG. 1 is an exploded view of an electrode matrix formed in accordance with the present invention;

FIG. 2 is a sectional view of the assembled electrode matrix of FIG. 1 provided with electrolyte gel;

FIG. 3 is a sectional view of an electrode packaging assembly for the electrode matrix of FIG. 2;

FIG. 4 is a sectional view of a second embodiment of an electrode depolarizing assembly of the present invention; and FIG. 5 is a sectional view of a third embodiment of an electrode depolarizing assembly of the present invention.

BEST MODE FOR CARRYING OUT THE INVENTION

Referring now to FIGS. 1 and 2, a pre-gelled biopotential electrode matrix indicated generally at 10 is formed in a manner which particularly adapts it for use in an electrode matrix depolarizing assembly formed in accordance with the present invention. The electrode matrix 10 includes a central substrate 12 which consists of a sheet of Mylar or other flexible, electrical insulating material, with electrodes 14 and electrical conductors 16 for each electrode applied as overlying layers on one surface of the substrate. The electrodes 14 may be positioned on the substrate in any desired number or configuration required for a specific biopotential mapping or screening use. These electrodes may be formed of any suitable conductive metal commonly used for biopotential electrodes but for purposes of description herein, the electrodes will be described as silver/silver chloride electrodes. The electrodes 14 are formed by first depositing a layer of silver onto the substrate 12, and at the same time, the leads 16, each of which contacts one of these silver layers, are deposited to provide conductors for the electrodes. These leads may also be formed of silver, although other electrically conductive materials such as copper may also be employed. A silver chloride layer is then deposited over the silver layer at each electrode location to form the basic silver/silver chloride layers for the electrode.

Although electroplating or deposition is one method for forming the electrodes 14 and leads 16 on the substrate 12, other methods commonly known to the printed circuit art may be employed. For example, the necessary compositions to form the electrodes and electrode leads may be coated on the substrate 12 by a brush coating or screen printing process as an alternative to electrode deposition. In all cases, the result will be a plurality of biopotential electrodes arranged in a pattern on a flexible, insulating substrate with conductive leads extending outwardly to one edge of the substrate.

To support the substrate 12 and to permit the electrode matrix to be shipped and stored in a pre-gelled state, the substrate is mounted between two thin sheets of foam or other insulating material 18 and 20. The sheet 20 is a solid backing sheet, while the sheet 18 is a face sheet which is formed with a plurality of punched or die-cut holes 22 extending therethrough. The holes 22 are positioned to correspond with the electrodes 14 when the face sheet 18 is placed into position over the substrate 12. It will be noted that the face sheet 18 and the backing sheet 20 are cut to be shorter than the substrate 12 so that an end 24 of the substrate where the electrical leads 16 terminate projects outwardly from the electrical insulating foam face and backing sheets as shown in FIG. 2. In some instances, it is possible for only one of the sheets on the side of the substrate bearing the electrical leads to be cut short, and in this case, it would be the sheet 18.

Once the face and backing sheets 18 and 20 are in position, the holes 22 are filled with electrolyte gel 26 to provide a pre-gelled electrode matrix. Thus, the silver chloride layer of each of the electrodes 14 is in contact with the electrolyte gel, and the unit is now in condition for depolarization.

To depolarize the pre-gelled electrode matrix 10 in accordance with the present invention, the electrical lead 16 for each electrode must be electrically connected with the electrolyte gel 26 which covers that specific electrode. This can be accomplished with separate electrically conductive strips extending between each individual electrode lead and the gel covering the electrode, but ideally, all electrodes in a matrix may be depolarized by a single conductive sheet, such as the sheet 28 in FIG. 3, which contacts all of the leads 16 and then extends into contact with the electrolyte gel covering each electrode. It is important for the conductive, depolarizing element, whether it is a conductive sheet or a single strip, to be an inert material which does not cause the electrolyte gel to degrade. This is especially true when the depolarizing element is a sheet which constitutes part of a packaging assembly, such as that shown in FIG. 3, for in this form the depolarizing element can be in contact with the gel for extensive periods while the pre-gelled electrode matrix 10 is shipped and stored prior to use.

In the formation of the package of FIG. 3, an electrically conductive sheet 28 is engaged with the surface of the face plate 18 so as to close the holes 22 and contact the gel 26 in each of these holes. This same conductive sheet extends out over the end of the foam sheet 18 and then down into contact with the projecting ends of the electrical leads 16 on the end 24 of the substrate. Thus, the electrolyte gel is connected by a direct electrical connection to the leads 16 to thereby provide a direct short circuit for the potentials generated by the battery effect provided by the pre-gelled electrode structure. In effect, the electrically conductive sheet 28 shorts out the opposed terminals of the battery thereby depolarizing the electrode matrix. This electrically conductive sheet can be a conductive Mylar TM sheet or any suitable electrically conductive sheet which will provide a direct conductor between the electrolyte gel and the electrical leads 16 without causing degradation of the electrolyte. Thus, the sheet 28 is preferably an inert conductive sheet, such as a carbon impregnated Mylar TM sheet, which will not cause either chemical or electrical degradation of the gel. Once this conductive sheet is in place, the electrode may be packaged in any suitable, non-conductive outer wrap or packaging configuration 30 to protect the electrode matrix in storage and shipment.

The electrode matrix packaging assembly of FIG. 3 effectively depolarizes the biopotential electrodes in the matrix so that a depolarized matrix is available at the time of use. At this time, the packaging material 30 and the electroconductive sheet 28 will be removed and the electrode will be used immediately.

As illustrated by FIG. 4, the present invention may be used with conventional pre-gelled biopotential electrodes in either individual or matrix form to depolarize the electrode prior to use. The invention is not limited to the combination of the depolarizing element with a packaging assembly, although this is an effective method for constructing the element. In FIG. 4, a single electrode indicated generally at 32 is mounted upon a support member 34 which may be a ring of plastic foam material or other material which forms an insulating cup. The electrode may include a silver layer 36 and a silver chloride layer 38 which are mounted in an insulating cup 40 formed by the support member 34. An electrolyte gel 42 is placed in contact with the silver chloride layer 38 to provide a pre-gelled electrode.

The electrode 32 includes a projecting snap button cable connection 44 which is in electrical contact with the silver layer 36 and which is designed to snap onto an electrical lead to a measuring and indicator unit. This is obviously a conventional pre-gelled electrode structure and is used as illustrative of a number of conventional pre-gelled biopotential electrodes with which the depolarizing structure of the present invention can be effectively employed.

To depolarize a single biopotential electrode of the type shown in FIG. 4, an electrically conductive material 46 is provided which is of sufficient size to contact the cable connector or terminal 44 and then to pass around one end of the support 34 across the opposite side of the assembly into contact with the electrolyte gel 42. This conductive material, which may be the same as that forming the sheet 28 in FIG. 3, provides an electrical path between the terminal 44 and the electrolyte gel for the biopotential electrode to provide a short circuit path therebetween. For example, the conductive material 46 may be formed by a Mylar outer layer 48 which supports an inert conductive coating layer 50. A pressure releasable adhesive is provided between the layer 50 and the support member 34 to hold the conductive material 46 in place but to permit its removal by means of a pull tab 52.

In FIG. 4, electrical contact is made between the terminal 44 and the conductive material 50, by an aperture 54 in the conductive material 46 which snaps over and receives the terminal. Once the conductive material is in place, suitable outer packaging material, such as the packaging material 30, can be placed over and around both ends of the unit to completely enclose the unit. This packaging material is a non-electrically conductive material which encloses the conductive material and the electrode.

With a single electrode, the conductive material 46 may be in the form of a elongated strip extending between the electrolyte and the terminal. Preferably, the strip is of sufficient width to cover the cup 40 to both enclose the gel and to provide maximum contact therewith. For purposes of illustration, the electrodes herein have been described as silver/silver chloride electrodes, and the electrolyte gel used might be sodium or potassium chloride. However, any suitable metal and electrolyte combination commonly used to form biopotential electrodes could be employed with the present invention.

FIG. 5 illustrates a very desirable structure for shorting pre-gelled electrodes during shipment and storage prior to use. This structure, indicated generally at 56 includes two pre-gelled electrodes 58a and 58b mounted back to back and held together by a nonconductive carrier 60 of Mylar or similar material. The Mylar carrier 60 extends between the electrodes 58a and 58b and permits subsequent separation of the electrodes. Holes 61 formed in the Mylar permit full contact between the electrolyte gel in the electrode 58a and the gel in the opposing electrode 58b. The components of each electrode will be given the same reference numbers differentiated by the letters "a" and "b".

The electrodes include a support member 62 which forms an insulating cup 64 open at one end 66 and which receives electrolyte gel 68. The carrier 60 extends across the open ends of the support members for each electrode and is provided with the openings 61 which permit the gel 68 in each electrode to make electrical contact with the gel in the opposing electrode. These openings should be as large as possible to permit full contact between the electrolyte gels 68a and 68b while still facilitating the subsequent separation of the electrodes 58a and 58b.

In contact with the electrolyte gel in each insulating cup is an electrode element 72 having a projecting snap button cable connector or terminal 74 for connection to an external cable. Each electrode element 72 may include a silver layer 76 and a silver chloride layer 78 or other conventional electrode element forming materials.

The structure 56, due to its configuration, constitutes a true battery and this battery is electrically short circuited during shipment and storage by a conductive wire or strip 80 electrically connected between the terminals 74a & b. This conductive wire or strip shorts the potential battery and brings the electrode elements to a stable, near zero volt DC level. Prior to use, the conductive wire or strip 80 is removed and the electrodes 58, now at near a zero DC level, are separated from the carrier 60 and immediately placed on a patient for bioelectric measurement purposes. After the wire or strip is removed, the electrodes should be promptly used, for if they are left unshorted they may once again develop unwanted DC offset potentials.

INDUSTRIAL APPLICABILITY

The electrode depolarizing structures of the present invention operate effectively to permit shipment and storage of biopotential electrodes in a pre-gelled condition while negating the battery effect normally present with such electrodes. The electrodes are effectively short circuited by an electrical conductor which may constitute part of the packaging assembly for the pre-gelled electrode and which is easily removed prior to electrode use. Once the conductor is removed, an unpolarized electrode structure is provided which will sense biopotentials.

We claim:

1. The pre-gelled electrode assembly for sensing biopotentials present in a living subject which is depolarized before use to reduce DC offset voltage which may be produced by said assembly to a substantially zero volt DC level comprising a base, at least a first electrode mounted upon said base for conducting a biopotential from said electrode assembly, electrolyte means for providing an electroconductive material mounted in contact with said first electrode and depolarizing means for creating an electrical short circuit path mounted to contact said electrolyte means in a contact area thereof which is spaced from said first electrode, said depolarizing means operating to form an electrical short circuit path between said contact area and said first electrode and including an electrically conductive means for completing said electrical short circuit path and which is removed from said electrode assembly before use to break said electrical short circuit path.

2. The electrode assembly of claim 1, wherein said electrically conductive means is formed of material which is insert relative to said electrolyte means to avoid degradation of said electrolyte means.

3. The electrode assembly of claim 1 wherein said electrically conductive means includes a sheet of conductive material contacting and covering said electrolyte means and contacting said first electrode.

4. The electrode assembly of claim 3, wherein said sheet of conductive material includes an inert conductive material.

5. The electrode assembly of claim 1, which includes a plurality of electrodes mounted in spaced relationship on said base, a separate conductive terminal connected to each such electrode and spaced from the conductive terminals connected to the remaining electrodes, and said electrolyte means including electrolyte contacting each said electrode.

6. The electrode assembly of claim 5, wherein said electrically conductive means includes a single sheet of conductive material covering said electrolyte means and contacting said conductive terminals, said electrolyte means including electrolyte contacting each such electrode and spaced by said base from the electrolyte contacting the remaining electrodes.

7. The electrode assembly of claim 6, wherein said base is formed from flexible, electrical insulating material.

8. The electrode assembly of claim 6, wherein said electrodes and conductive terminals are applied as overlying layers on a surface of said base, said conductive terminals extending in spaced relationship from said electrodes to spaced terminal points on said base.

9. The electrode assembly of claim 8, wherein a face sheet is mounted in contact with said base, said face sheet having a plurality of spaced apertures extending therethrough and each aperture being positioned to overlie an electrode when said face sheet is mounted on said base, said electrolyte being mounted in said spaced apertures.

10. The electrode assembly of claim 9, wherein said single sheet of conductive material is positioned to close said apertures.

11. The electrode assembly of claim 10, wherein said face sheet is formed to expose the terminal points of said conductive terminals, said sheet of conductive material contacting said terminal points.

12. The electrode assembly of claim 11, wherein said base is formed from flexible, electrical insulating material.

13. The electrode assembly of claim 12, wherein a backing sheet is mounted in contact with the said base, said base being positioned between said face and backing sheets.

14. The electrode assembly of claim 1 wherein said base includes at least one chamber receiving and containing said electrolyte means, said first electrode being mounted in said chamber in contact with said electrolyte means, and an electrical terminal means for conducting a potential from said first electrode, said electrically conductive means extending externally of said chamber to said electrical terminal means.

15. The electrode assembly of claim 14 wherein said chamber includes an opening spaced from said first electrode, said electrically conductive means extending into said opening in contact with said electrolyte means.

16. The electrode assembly of claim 15 wherein said electrically conductive means includes a first section which extends across and closes said opening, said electrically conductive means extending externally of said base between said opening and said electrical terminal means.

17. The electrode assembly of claim 1 wherein said base includes at least first and second support means for forming electrolyte receiving chambers, each such support means including a chamber open at one end to receive said electrolyte, said first electrode being mounted in the chamber of said first support means in contact with the electrolyte therein and in spaced relation to the open end thereof, said depolarizing means including a second electrode mounted in the chamber of said second support means in contact with the electrolyte therein and in spaced relation to the open end thereof, the open ends of said first and second chambers being mounted in opposed juxtaposition wherein the electrolyte in said first chamber is in contact with the electrolyte in said second chamber, said removably mounted electrically conductive means being connected to create an electrical short circuit path between said first and second electrodes.

18. The electrode assembly of claim 17 wherein said base is formed to permit said first support means to be separated from said second support means to form at least two separate electrode units, each electrode unit containing electrolyte and one of said electrodes.

19. The electrode assembly of claim 18 wherein a separate sheet is provided between said first and second support means and is mounted over the open ends of the chambers formed therein, said separation sheet including at least one opening to permit the electrolyte in said chamber of said first support means to contact the electrolyte in the chamber of said second support means.

20. The electrode assembly of claim 19 wherein each of said first and second electrodes includes a terminal which extends outwardly form the chamber in which said electrode is mounted, said electrically conductive means having at least a first section removably mounted on the terminal for either said first or said second electrode.

21. An electrode assembly comprising a substrate, electrode means for sensing biopotentials mounted upon said substrate, said electrode means including a plurality spaced electrodes deposited as a coating on one surface of said substrate, electrically conductive lead means for conducting a potential from said electrode mans mounted upon said substrate and connected to said electrode means, said electrically conductive lead means including an electrical lead for each electrode deposited as a coating on one surface of said substrate, an electrolyte in contact with each of said spaced electrodes, containment means for receiving said electrolyte and electrode means, said containment means including a face sheet having a plurality of spaced apertures extending therethrough mounted to contact said substrate, each aperture being positioned to overlie an electrode when said face sheet is mounted in contact with said substrate, said electrolyte being mounted in said spaced apertures, and electrically conductive means for closing said apertures contacting said electrolyte in an area spaced form said electrodes, said electrically conductive means extending between said electrolyte and said electrically conductive lead means to depolarize said electrode assembly.

22. The electrode assembly of claim 21 wherein said face sheet is a sheet of electrical insulating material, said electrically conductive means including a sheet of electrically conductive material overlying said face sheet and contacting said electrically conductive lead means.

23. The electrode matrix assembly of claim 22, wherein said face sheet is formed of an electrically insulating foam material, said substrate being formed of a flexible sheet of electrical insulating material, and said sheet of electrically conductive material being formed by a sheet of material which is insert relative to said electrolyte to avoid degradation thereof.

24. A pre-gelled, depolarized electrode assembly comprising first and second electrode units, each of said electrode units including at least one electrode means for sensing and conducting a biopotential, an electrolyte, support means for mounting said electrode means and said electrolyte in contact with said electrode means, conductor means spaced from said electrolyte for conducting a potential from said electrode means, mounting means for mounting said first and second electrode units with the electrolyte of said first electrode unit in electrical contact with the electrolyte of said second electrode unit and electrically conductive means for providing a short circuit connection mounted in contact with the conductor means of said first and second electrode units and extending therebetween.

25. The electrode assembly of claim 24 wherein the mounting means mounts said first and second electrode units with the electrolyte of said units in direct physical contact.

26. The electrode assembly of claim 25 wherein said mounting means includes a separation sheet extending between said first and second electrode units, said separation sheet including at least one opening to permit the electrolyte of said first electrode unit to contact the electrolyte of said second electrode unit.

27. The electrode assembly of claim 26 wherein said support means forms an open ended chamber to receive said electrolyte, said separation sheet extending across the open end of the open ended chambers of said first and second electrode units.

28. The electrode assembly of claim 24 wherein said support means forms a chamber with an open end to receive said electrolyte, said mounting means operating to mount the open end of the chamber of said first electrode unit in juxtaposition with the open end of the chamber of said second electrode unit.

29. A pre-gelled, depolarized electrode assembly comprising containment means for forming a chamber to receive and contain an electrolyte, an electrolyte contained in said chamber, first electrode means for conducting an electrical potential mounted within said chamber in contact with said electrolyte, first electrical terminal means connected to said first electrode means and extending outwardly of said chamber for conducting a potential from said first electrode means, and means for making electrical contact with said electrolyte in an area thereof which is spaced form said first electrode means, said means for making electrical contact including removably mounted electrical conductive means operative to provide a short circuit electrical connection form said area of contact with said electrolyte to said first electrical terminal means, said electrical conductive means extending externally of said chamber to said first electrical terminal means.

30. The pre-gelled, depolarized electrode assembly of claim 29 wherein said means for making electrical contact with said electrolyte in the area thereof spaced from said first electrode means includes a second electrode means for conducting an electrical potential mounted within said chamber in contact with said electrolyte in said area thereof spaced form said first electrode means and second electrical terminal means extending outwardly of said chamber for conducting a potential from said second electrode means, said electrical conducive means being removably mounted on said first and second electrical terminal means and extending therebetween externally of said chamber.

31. The pre-gelled, depolarized electrode assembly of claim 30 wherein said containment means is formed to separate into two parts, each part containing electrolyte and one of said first and second electrode means.

32. A depolarized electrode assembly for sensing biopotentials present in a living subject through contact with the skin of the subject which is depolarized before use to reduce DC offset voltages which may be produced by said assembly to a substantially zero volt DC level comprising at least first and second electrode units, each of which includes an electrode for conducting a biopotential form the electrode unit and contact means in contact with the electrode for contacting the skin of a subject to facilitate ion migration between the skin and the electrode, said first and second electrode units being mounted in opposed relationship with the contact means of said first electrode unit in contact with the contact means of said second electrode unit, and electrically conductive means mounted to create an electrical short circuit path between the electrodes of said first and second electrode units, said electrically conductive means being formed to facilitate the breaking of said short circuit path prior to the use of said first and second electrode units.

33. A method for depolarizing a pre-gelled electrode assembly having at least first and second spaced electrodes in contact with an electrolyte which extends between said electrodes, the method including the step of creating a low impedance electrical path between said first and second spaced electrodes so as to be electrically isolated from said electrolyte and maintaining said low impedance electrical path between said first and second electrodes until DC voltage level measured across said electrodes reaches a stable, substantially zero volt DC level.

34. A method for depolarizing a pre-gelled electrode assembly having at least one electrode in contact with an electrolyte to create a DC offset voltage which includes the steps of creating a low impedance electrical path between said electrode and a portion of said electrolyte which is spaced from said electrode and maintaining said low impedance electrical path until the DC offset voltage of said electrode assembly reaches a stable, substantially zero volt DC level.

* * * * *